(12) United States Patent
Wang et al.

(10) Patent No.: US 10,232,382 B2
(45) Date of Patent: Mar. 19, 2019

(54) WIRELESS SWNT SENSOR INTEGRATED WITH MICROFLUIDIC SYSTEM FOR VARIOUS LIQUID SENSING APPLICATIONS

(71) Applicant: Northeastern University, Boston, MA (US)

(72) Inventors: Ming Wang, Stoneham, MA (US); Yu Liu, Boston, MA (US); Mehmet Remzi Dokmeci, Brookline, MA (US)

(73) Assignee: Northeastern University, Boston, MA (US)

( * ) Notice: Subject to any disclaimer, the term of this patent is extended or adjusted under 35 U.S.C. 154(b) by 407 days.

(21) Appl. No.: 14/974,517

(22) Filed: Dec. 18, 2015

(65) Prior Publication Data

US 2016/0129455 A1 May 12, 2016

Related U.S. Application Data

(62) Division of application No. 13/738,658, filed on Jan. 10, 2013, now abandoned.

(Continued)

(51) Int. Cl.
*B82Y 15/00* (2011.01)
*B03C 5/00* (2006.01)
(Continued)

(52) U.S. Cl.
CPC ............ *B03C 5/005* (2013.01); *A61B 5/1473* (2013.01); *B01L 3/50273* (2013.01);
(Continued)

(58) Field of Classification Search
None
See application file for complete search history.

(56) References Cited

U.S. PATENT DOCUMENTS

2007/0048181 A1 3/2007 Chang et al.
2008/0063566 A1 3/2008 Matsumoto et al.
(Continued)

FOREIGN PATENT DOCUMENTS

WO WO 2010044932 A2 4/2010

OTHER PUBLICATIONS

Lei et al., "Simple graphene chemiresistors as pH sensors: fabrication and characterization," Measurement Science and Technology, vol. 22, 6 pages (2011).
(Continued)

*Primary Examiner* — Erik B Crawford
(74) *Attorney, Agent, or Firm* — Arent Fox LLP (57) ABSTRACT

Sensors based on single-walled carbon nanotubes (SWNT) are integrated into a microfluidic system outfitted with data processing and wireless transmission capability. The sensors combine the sensitivity, specificity, and miniature size of SWNT-based nanosensors with the flexible fluid handling power of microfluidic "lab on a chip" analytical systems. Methods of integrating the SWNT-based sensor into a microfluidic system are compatible with the delicate nature of the SWNT sensor elements. The sensor devices are capable of continuously and autonomously monitoring and analyzing liquid samples in remote locations, and are applicable to real time water quality monitoring and monitoring of fluids in living systems and environments. The sensor devices and fabrication methods of the invention constitute a platform technology, because the devices can be designed to specifically detect a large number of distinct chemical agents based on the functionalization of the SWNT. The sensors can be combined into a multiplex format that detects desired combinations of chemical agents simultaneously.

6 Claims, 8 Drawing Sheets

Related U.S. Application Data (60) Provisional application No. 61/584,857, filed on Jan. 10, 2012.

(51) Int. Cl.
| | |
|---|---|
| *A61B 5/1473* | (2006.01) |
| *G01N 27/02* | (2006.01) |
| *H01L 21/02* | (2006.01) |
| *G01N 33/18* | (2006.01) |
| *B01L 3/00* | (2006.01) |
| *G01N 27/07* | (2006.01) |
| *G01N 27/414* | (2006.01) |

(52) U.S. Cl.
CPC ............ *G01N 27/02* (2013.01); *G01N 27/07* (2013.01); *G01N 33/18* (2013.01); *H01L 21/02104* (2013.01); *B01L 2200/10* (2013.01); *B01L 2300/023* (2013.01); *B01L 2300/0645* (2013.01); *B01L 2300/0816* (2013.01); *B01L 2300/0896* (2013.01); *B01L 2400/0406* (2013.01); *B01L 2400/049* (2013.01); *B01L 2400/0439* (2013.01); *B82Y 15/00* (2013.01); *G01N 27/4146* (2013.01)

(56) References Cited

U.S. PATENT DOCUMENTS

| | | |
|---|---|---|
| 2008/0093226 A1 | 4/2008 | Briman et al. |
| 2008/0182301 A1 | 7/2008 | Handique et al. |
| 2010/0038794 A1 | 2/2010 | Busnaina et al. |
| 2010/0282617 A1 | 11/2010 | Rothberg et al. |
| 2011/0227558 A1 | 9/2011 | Mannion et al. |
| 2012/0134880 A1 | 5/2012 | Kurkina et al. |
| 2014/0331930 A1* | 11/2014 | Freer .................. B82Y 10/00 118/697 |

OTHER PUBLICATIONS

Kaempgen et al., "Transparent and flexible carbon nanotube/polyaniline pH sensors," Journal of Electroanalytical Chemistry, vol. 586, pp. 72-76 (2006).

Rawson et al., "Electron transfer from Proteus vulgaris to a covalently assembled, single walled carbon nanotube electrode functionalised with osmium bipyridine complex: Application to a whole cell biosensor," Biosensors and Bioelectronics, vol. 26, pp. 2383-2389 (2011).

Roberts et al., "Sorted and Aligned Single-Walled Carbon Nanotube Networks for Transistor-Based Aqueous Chemical Sensors," American Chemical Society, vol. 3, No. 10, pp. 3287-3293 (2009).

Forzani et al., "Tuning the Chemical Selectivity of SWNT-FETs for Detection of Heavy-Metal Ions," small journal, vol. 2, No. 11, pp. 1283-1291 (2006).

Zhou et al., "Bacteria capture, concentration and detection by alternating current dielectrophoresis and self-assembly of dispersed single-wall carbon nanotubes," Electrophoresis Journal, vol. 27, pp. 1376-1385 (2006).

Bhattacharya et al., "Carbon nanotube based sensors for the detection of viruses," Sensors and Actuators B, vol. 155. pp. 67-74 (2011).

Fu et al., "Integrated Single-Walled Carbon Nanotube/Microfluidic Devices for the Study of the Sensing Mechanism of Nanotube Sensors," Journal of Physical Chemistry B, vol. 109, No. 28, pp. 13406-13408 (2005).

Bourlon et al., "A nanoscale probe for fluidic and ionic transport," Nature Nanotechology, vol. 2, pp. 104-107 (2007).

Selvarasah et al., "A reusable high aspect ratio parylene-C shadow mask technology for diverse micropatterning applications," Sensors and Actuators A, vol. 145-146, pp. 306-315 (2008).

Zhao et al., "Functionalization of carbon nanotubes with a pH-responsive molecule to produce a pHsensor," Nanotechnology, vol. 20, 6 pages (2009).

* cited by examiner

WIRELESS SWNT SENSOR INTEGRATED WITH MICROFLUIDIC SYSTEM FOR VARIOUS LIQUID SENSING APPLICATIONS

CROSS-REFERENCE TO RELATED APPLICATIONS

This application is a divisional of U.S. application Ser. No. 13/738,658, filed 10 Jan. 2013. This application also claims the priority of U.S. Provisional Application No. 61/584,857 filed Jan. 10, 2012 and entitled "Wireless SWNT Sensor Integrated With Microfluidic System for Various Liquid Sensing Applications", the whole of which is hereby incorporated by reference.

STATEMENT REGARDING FEDERALLY SPONSORED RESEARCH OR DEVELOPMENT

The invention was developed with financial support from Grant No. 0731102 from the National Science Foundation. The U.S. Government has certain rights in the invention.

BACKGROUND

Pollutants in water have significant impact on human health and the natural environment. Environmental contamination, such as high levels of nutrients, industrial wastes, toxic chemicals, and algal blooms can lead to mass mortality in fish and seabirds and may possibly result in disease outbreaks. Conventional water quality evaluation is typically conducted by on-site sampling followed by transport to a laboratory for testing, or on-site data collection. Such procedures are costly, time consuming, and require skilled operators. Further, the test results can only indicate the quality of water at the specific time and location of sampling. Water quality preferably should be monitored in a fast and efficient manner and in real time which allows the responses to be used to adequately address the sources of water contamination as quickly as possible. Recent developments have shown a trend toward continuous data collection using in situ detectors [1].

Carbon nanotubes have a high aspect ratio, large surface area, and unique electrical properties that offer great potential in chemical and biological sensing applications [2, 3]. Nanotube based sensors exhibit fast response (less than 5 seconds in response to pH buffers [4]), high sensitivity (down to 20 ppb in response to dimethyl methylphosphonate in water [5]) and are miniature in size. As an essentially one-dimensional nanomaterial composed of a single atomic layer, single-walled carbon nanotubes (SWNT) are extremely sensitive to chemical and environmental conditions, and the conductance of SWNTs can change dramatically when exposed to a low concentration of ions or molecules in liquid. Various SWNT sensors have been developed and utilized for liquid analysis, including sensors for pH value [4], heavy metal ions [6], toxic organics [5], bacteria [7], and viruses [8].

Microfluidics technology is being increasingly applied in chemical, biological and medical diagnostics of solution-based samples. Microfluidics offers numerous attractive features, such as the ability to use small amounts of samples or reagents; to carry out sample separations and detections with high resolution and sensitivity; to significantly reduce the cost per analysis; to replace batch analysis with continuous flow analysis; and to reduce the footprint of analytical devices [9]. Microfluidic systems are able to manipulate and examine samples containing a single cell or a single molecule [10], which is especially important for bioanalysis. Use of droplet fluidics is a new trend in microfluidics systems, which includes the control of the droplet volume, chemical concentrations within the droplet, and sorting of droplets based on flow pattern [11].

Integration of an SWNT sensor with a microfluidic system would enable the development of a lab-on-a-chip device that can perform water quality monitoring and other types of analysis of liquid samples. Such a chip would replace many types of measurement that are normally performed manually in a lab using bulky equipment. With a suitable design, the microfluidic system can carry out sample preparation steps, including filtering and separating various components in a liquid sample, and then guide the solution to a nanosensor array for analysis.

In order to develop a highly sensitive and autonomous microdevice for real-time in situ water quality monitoring, the SWNT sensors have to be integrated with the microfluidic system, e.g., on a single chip. Permanent bonding of a microfluidic channel onto a silicon substrate requires treatment with an oxygen plasma. However, such a plasma treatment of a carbon nanotube-based device would damage the nanotubes. Fu and colleagues integrated a SWNT sensor with a microfluidic channel by covering the SWNT with a continuous metal layer which protected the nanotubes underneath during exposure to oxygen plasma [12]. After bonding the SWNT device with a microfluidic channel made of polydimethylsiloxane (PDMS), an etching solution was introduced through the channel to remove the metal mask layer covering the SWNT, so that the SWNT inside the microfluidic channel could be used for sensing applications [12]. However, this type of integration process could introduce contamination onto the SWNT from the etching solution and the substances generated by the chemical reactions. Bourlon and colleagues have fabricated a flow and ionic sensor using a nanotube transistor covered with a PDMS channel without using an oxygen plasma treatment [13]; however, the microfluidic channel was not well sealed on the device which resulted in leakage of solution. Thus, there remains a need to develop procedures and devices that incorporate SWNT into microfluidic channels without compromising the integrity of the SWNT or the fluid handling of the microfluidics system.

SUMMARY OF THE INVENTION

The present invention integrates the sensitivity, specificity, and miniature size of SWNT-based sensors with the flexible fluid handling power of microfluidic "lab on a chip" analytical systems. The further addition of data analysis and wireless transmission capabilities results in a nanosensor device capable of either continuous or intermittent sampling and analysis of liquid samples, especially in remote or poorly accessible locations. The sensor device is directly applicable to water quality monitoring and bioanalytical monitoring in living systems. The methods of fabricating microfluidic embodiments of the sensor device are compatible with the delicate nature of the sensor elements.

One aspect of the invention is a sensor device for the detection of a chemical agent in a liquid sample. The device includes a substrate, a patterned conductive layer deposited on a surface of the substrate and forming first and second microelectrodes with a gap between the microelectrodes, a nanosensor connected to the microelectrodes and traversing the gap, and a microfluidic channel that contains the nanosensor within its lumen. The nanosensor includes one or more single-walled carbon nanotubes (SWNT) that have been assembled across the microelectrodes using dielectrophoresis. In some embodiments, the SWNT have been functionalized so as to provide a change in an electrical property of the SWNT in response to a particular chemical agent or analyte. In some embodiments, the microfluidic channel defines a fluid pathway that connects the lumen containing the nanosensor with an inlet port and an outlet port, through which the liquid sample for analysis is added to and removed from the device, respectively. The ports can be on any surface of the device, including the substrate, the conductive layer, or a housing for the device. Optionally, the microelectrodes, or portions of the conductive layer connected with them, are connected to a detection circuit formed by part of the conductive layer or mounted on the substrate. The detection circuit applies a voltage across the SWNT sensor element through the microelectrodes, detects a change in an electrical property of the SWNT in response to binding of the chemical agent to the SWNT or a functional group on the SWNT. The change in electrical property is preferably a change in resistance or capacitance of the SWNT. The detection circuit then produces an output signal, such as a voltage, that is related to the presence and/or amount or concentration of the chemical agent in the test sample.

Another aspect of the invention is a method of fabricating the sensor device described above. The method includes the steps of: (a) depositing a conductive layer onto an insulating or semiconducting substrate, whereby the conductive layer forms a pattern that includes first and second microelectrodes and having a gap between the first and second microelectrodes; (b) forming a microfluidic channel that covers a portion of the substrate, encloses the gap, and is fluidically connected on one side of the gap to an inlet port and on another side of the gap to an outlet port; (c) flowing an aqueous suspension of SWNT through the inlet port to fill the enclosed gap with the aqueous suspension; (d) applying an AC voltage between the first and second microelectrodes, whereby SWNT are dielectrophoretically assembled across the gap and form an electrical connection at one end of the SWNT with the first microelectrode and at another end of the SWNT with the second microelectrode; and (e) removing the aqueous suspension of SWNT from the microfluidic channel.

Yet another aspect of the invention is another method of fabricating the above-described sensor device. The method includes the steps of: (a) depositing a conductive layer onto an insulating or semiconducting substrate, whereby the conductive layer forms a pattern comprising first and second microelectrodes and having a gap between the first and second microelectrodes; (b) depositing an aqueous suspension of SWNT onto the substrate so as to cover the gap between the first and second microelectrodes with the aqueous suspension; (c) applying an AC voltage between the first and second microelectrodes, whereby SWNT are dielectrophoretically assembled across the gap and form an electrical connection at one end of the SWNT with the first microelectrode and at another end of the SWNT with the second microelectrode; (d) removing said aqueous suspension of SWNT from the substrate; (e) forming a parylene shadow mask covering the assembled SWNT; (f) plasma treating the substrate; (g) removing the shadow mask; and (h) bonding a microfluidic channel to the substrate that encloses the gap and the assembled SWNT, and is fluidically connected on one side of the gap to an inlet port and on another side of the gap to an outlet port.

Still another aspect of the invention is a method of detecting or quantifying a chemical agent in a liquid sample. The method includes the steps of: (a) providing the above-described sensor device; (b) flowing the liquid sample into the inlet port of the sensor device so as to fill the enclosed gap; and (c) observing an output signal from the detection circuit of the sensor device. The observed output signal indicates the presence or absence of, and/or the amount or concentration of the chemical agent.

BRIEF DESCRIPTION OF THE DRAWINGS

FIGS. 2(a)-2(d) show an embodiment of a fabrication process for integrating SWNT sensors inside a microfluidic channel.

FIGS. 3(a)-3(b) show scanning electron microscope (SEM) micrographs of SWNT assembled on Au microelectrodes. In FIG. 3(a), nanotube bundles are visible which are immobilized on the electrodes after assembly.

DETAILED DESCRIPTION OF THE INVENTION

The inventors have developed methods for integrating sensors based on single-walled carbon nanotubes (SWNT) into a microfluidic system, and optionally outfitting the integrated device with data processing and wireless transmission capability. The sensors combine the sensitivity, specificity, and miniature size of SWNT-based nanosensors with the flexible fluid handling power of microfluidic "lab on a chip" analytical systems. The methods developed can be used to fabricate new sensor devices by constructing a microfluidic system using techniques that are compatible with the delicate nature of the SWNT sensor elements. The microfluidic mechanism enables the sensor devices to continuously and autonomously monitor liquid samples for the presence or absence and/or concentration of desired chemical agents. The addition of wireless data transmission extends the capability of the sensor devices to real time remote sensing operations, sensing in remote locations, and sensing of selected fluid-containing spaces in living organisms. The sensor devices of the invention are well suited to continuous monitoring of water quality in the environment as well as in industrial and home settings. The sensor devices and fabrication methods of the invention provide a platform technology. Their specificity for detecting different chemical agents can be varied according to the functionalization of the SWNT used as the sensor element. Different sensors also can be combined in a multiplex format, so that desired combinations of chemical agents can be detected or analyzed simultaneously.

Figure 1A:
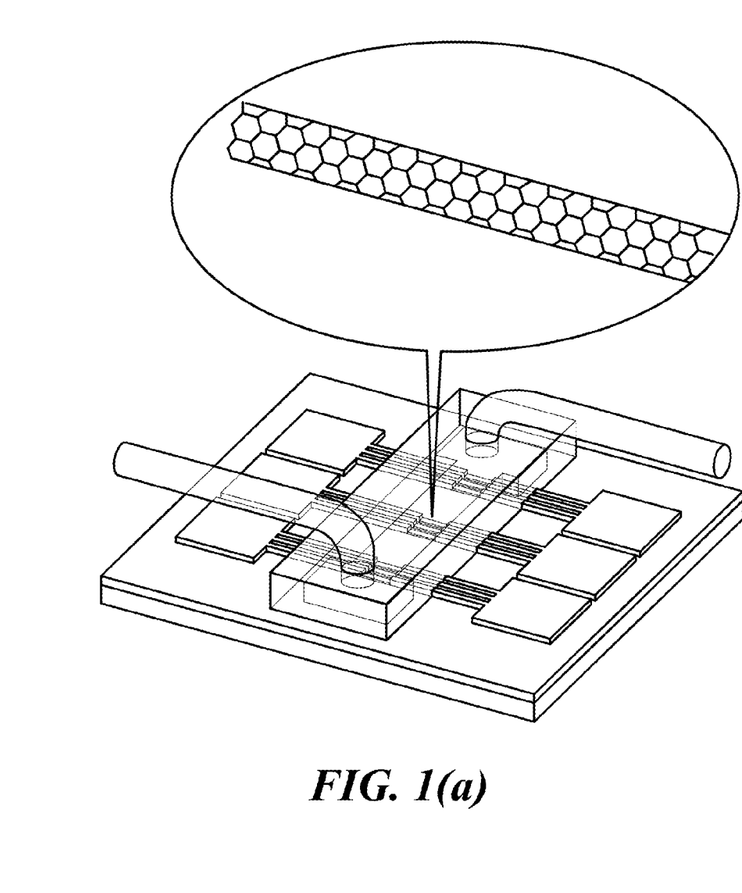
FIG. 1(a) shows a schematic illustration of an SWNT sensor inside a microfluidic channel for continuous flow-through monitoring of a liquid sample.

A schematic illustration of one embodiment of a nanotube-microfluidic sensor is presented in FIG. 1(a). The overall configuration of the sensor includes a substrate having a patterned conductive layer deposited on a surface of the substrate, and an attached microfluidic channel that encloses the sensor element on the substrate. The substrate is made from or contains an electrically insulating (non-conducting) or semiconducting material such as silicon, silicon oxide, glass, or a polymer such as a non-conducting organic polymer, or any combination thereof. The substrate is typically flat and rigid, but its shape and thickness can be chosen according to use. The substrate can also be flexible and either opaque or transparent. It can also be made of a biocompatible material. The surface area of the substrate can be selected by the user's requirements, but it can be quite small, even small enough to fit in a blood vessel of a mammal such as a human.

Figure 1B:
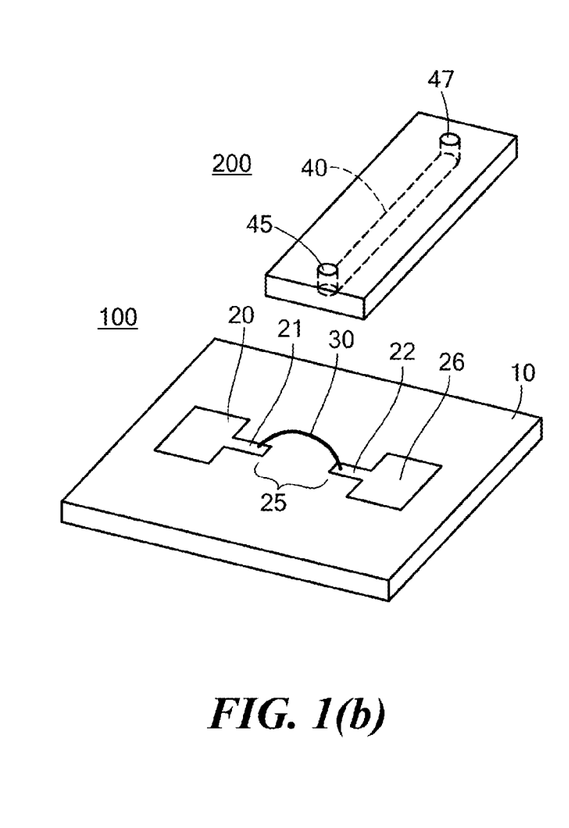
FIG. 1(b) shows a view of the sensor with the microfluidic channel removed.
Figure 2A:
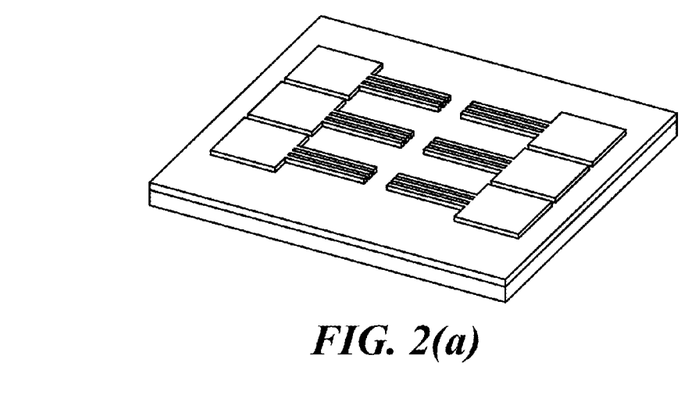
FIG. 2(a) shows the configuration of Cr/Au microelectrodes that were fabricated by photolithography on a $SiO_2$ substrate.
Figure 2B:
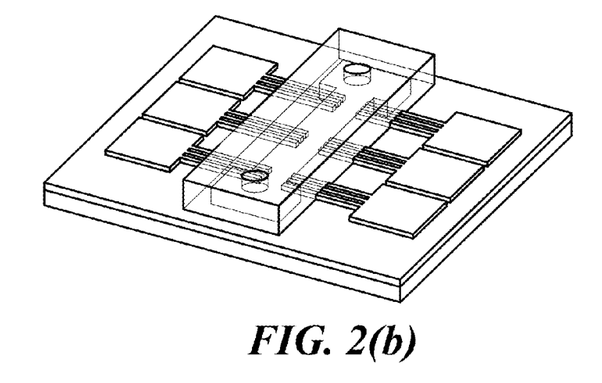
FIG. 2(b) shows a microfluidic channel that has been bonded onto the Si chip from FIG. 2(a).
Figure 2C:
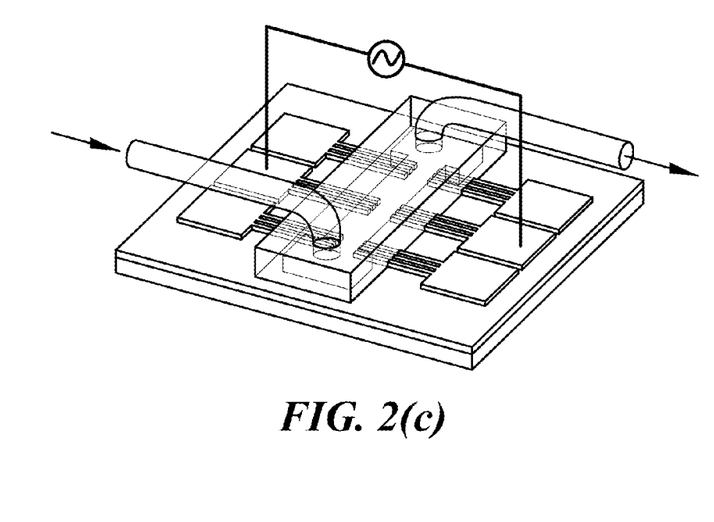
FIG. 2(c) illustrates how a dielectrophoretic process was utilized to assemble SWNT at appropriate location and with appropriate alignment inside the microfluidic channel. SWNT solution was transported to the electrodes inside the channel by the microfluidic system and an AC electric field was applied to the electrode pads outside the channel.
Figure 2D:
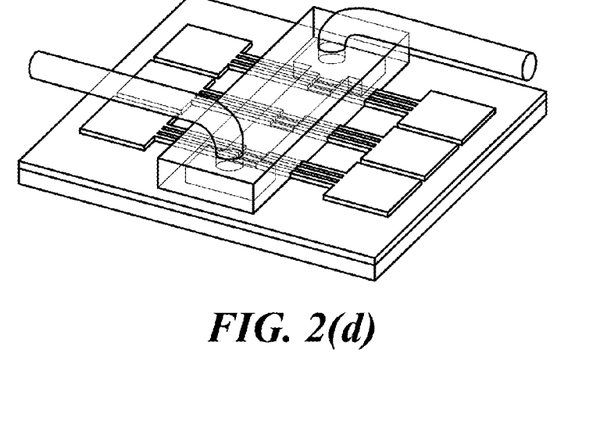
FIG. 2(d) shows the fabricated SWNT sensors integrated within the final microfluidic system.

In FIG. 1(b), microfluidic channel housing 200 is shown detached from the lower portion of sensor device 100. The microfluidic channel can be fabricated in any material known for use in microfluidics, such as polydimethylsiloxane (PDMS), glass, silicon, a polymer, or any combination thereof. The channel housing material is preferably hydrophilic, so that water and aqueous solutions can readily be transported through it with a minimum of resistance. The channel can be silanized or otherwise coated to reduce binding or adsorption of the analyte or interfering substances.

Substrate 10 is overlaid with a conductive layer which forms first microelectrode 21 and second microelectrode 22; the microelectrodes are linked via conductive pathways to contact pads 20 and 26, respectively, through which electrical contact is made with a detection circuit (not shown). The conductive layer can be formed by depositing a conductive material, e.g., by sputtering, chemical vapor deposition, or physical vapor deposition, and patterned using a lithography process. Suitable conductive materials include Au, Ag, Al, Cr, Cu, conductive polymers, metal particle composites, metal-polymer particle composites, nanotubes, and combinations thereof. The microelectrodes are each in electrical contact with one end of nanosensor 30, which contains one or more dielectrophoretically assembled SWNT. The microelectrodes are disposed on the substrate leaving a non-conductive gap between them. The gap can be filled with air, vacuum, or a non-conducting material. The gap is preferably on the order of about 1 µm to about 10 µm in length. The size of the gap is selected so as to be conveniently bridged by an assembly of one or more SWNT formed by a dielectric assembly process which involves establishing an AC voltage between the microelectrodes in the presence of an aqueous suspension of individual dispersed SWNT. Optionally, an AC voltage source can be combined with a DC offset voltage so that a combination of dielectrophoresis and electrophoresis is used for assembly. Methods for dielectric assembly of SWNT are well known in the art.

The SWNT used for dielectric assembly can be metallic SWNT, semiconducting SWNT, nonconducting or insulating SWNT (which can be added to adjust the electrical properties of the nanosensor, e.g., to adjust based on size of the sensor or type of functionalization), functionalized SWNT, non-functionalized SWNT, or any combination thereof. Functionalization of SWNT is well known in the art. For example, a glucose sensor can be fabricated using SWNT functionalized by coating them with the enzyme glucose oxidase. A sensor for a specific cell type, such as a bacterial species or strain, or a virus species or strain, can be fabricated using SWNT functionalized by coating with an antibody specific for the cell, bacterium, or virus. A sensor for a specific organic compound, such as a pollutant or toxin, can be fabricated using SWNT functionalized by coating with an antibody or a compound that binds with or reacts with the target compound. Non-functionalized SWNT are sensitive to $H^+$. SWNT can be assembled onto the first and second microelectrodes either in a pre-functionalized state, or they can be assembled in an already functionalized state. Pre-functionalized SWNT can be SWNT that have appropriate chemical substituents attached to the SWNT, such as —COOH, —$NH_2$, or —SH groups, and after assembly the specific binding or reacting agent (e.g., antibody) can be coupled to the SWNT, which are then functionalized in situ by introducing the appropriate reactants and reaction conditions using the microfluidic system.

Microfluidic channel 40 is a fluid passageway having inlet port 45 and outlet port 47 accessible from the side not attached to the substrate, and having an open space on the underside of the channel housing in position to enclose gap 25 between the microelectrodes and nanosensor element 30. The open space of the channel is fluidically connected with the inlet port on one side of the space and with the outlet port on the other side of the space, such that sample liquid can flow in through the inlet port, across the nanosensor element, and then out through the outlet port. The terms "inlet port" and "outlet port" do not require that the port have an opening at the surface of the microfluidics housing or the device housing, although it may. The port can also be a connection to another fluid channel or pathway within the device. Optionally, the fluid can be directed not to inlet and outlet ports but to one or more additional microfluidic channels, reservoirs, pumps, vacuum supply channels, reaction chambers, filters, or processing chambers on the same substrate or on an attached or separate microfluidic module or chip. Fluid can be moved through the microfluidic channel by any means known in the art of microfluidics, including the use if a pump (e.g., a piezoelectric device), capillary action alone, or vacuum applied through a port on the device attached to a vacuum source. Optionally, tubing can be attached to the inlet and/or outlet ports; the other end of the tubing can be placed into, for example, a sample fluid reservoir, a natural body of water or sampling fluid space, waste receptacle, syringe, or pump.

It should be noted that the sensor device can be configured as a single sensor, as a compound sensor having two or more iterations of a single type of sensor (either sharing common fluid sample pathways or each having its own fluid sample pathway), or as a multiplex sensor having two or more different types of sensor (e.g., each using differently functionalized SWNT and therefore sensitive to a different chemical agent).

The invention contemplates two different fabrication processes with which to integrate SWNT nanosensors into a microfluidic system. Both processes are efficient and result in high yield. The first approach is schematically illustrated in FIG. 2. Microelectrodes with a gap of 3 μm were fabricated by photolithography and metal deposition (Cr/Au, 20 nm/150 nm) on an oxidized silicon wafer (FIG. 2(a)). A PDMS slab embossed with a microfluidic channel (length/width/height: 8 mm/2 mm/150 μm) was cast using SU-8 replica molding which was created by photolithography [14]. The silicon chip with the microelectrodes and the microfluidic channel was exposed to an oxygen plasma (Plasma-Therm 790) for 30 seconds and then placed in contact with a hot plate at a temperature of 150° C. for 15 min (FIG. 2(b)). This process generated a permanent seal between the PDMS channel and the silicon chip [15]. Two holes were punched with a syringe needle on the microfluidic channel and Tygon tubes (Small Parts, Inc.) were inserted into the holes. The SWNT were next assembled between Au electrodes by a low temperature, dielectrophoresis (DEP) process inside the microfluidic channel (FIG. 2(c)). In this process, commercially available SWNT (diameter: 1-2 nm and length: 2-5 μm) in aqueous suspension at a concentration of 40 mg/L were injected into the microfluidic channel using a syringe. An AC field of 5 Vpeak-to-peak and 300 KHz was applied between the two electrodes for 1 min to assemble the nanotubes. After assembly, the remaining SWNT solution inside the microchannel was removed by injecting air into the channel. During dielectrophoretic assembly, carbon nanotubes were immobilized on Au electrodes by Van der Waals forces (FIG. 2(d)). I-V measurements confirmed the assembly of SWNT inside the microfluidic system.

Figure 3A:
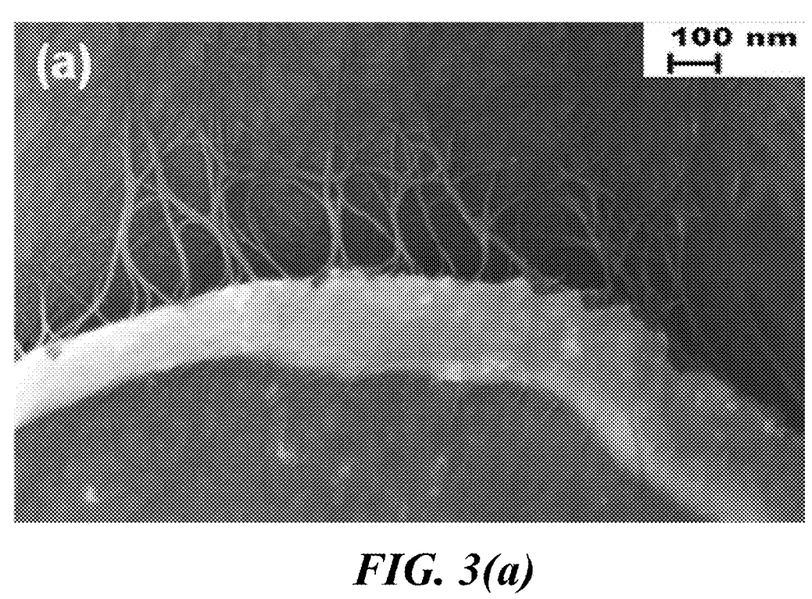
Figure 3B:
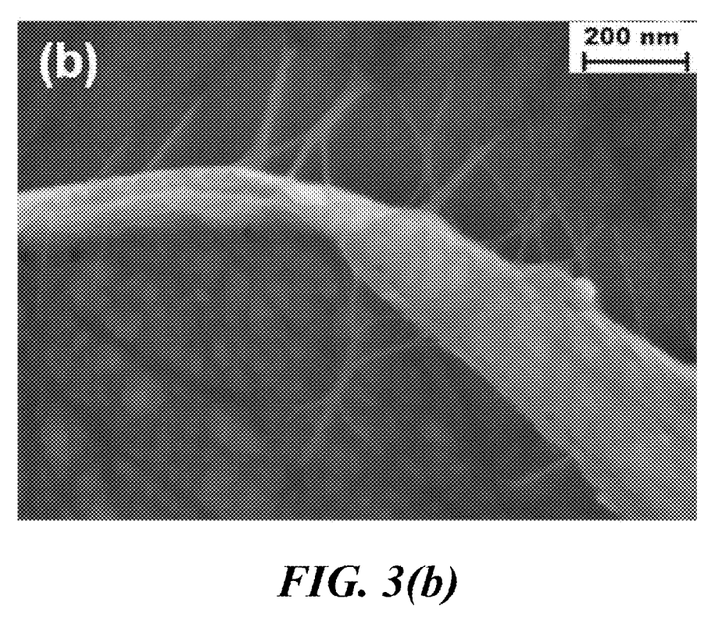
FIG. 3(b) shows SWNT assembled on a microelectrode after exposure to oxygen plasma protected with a parylene mask. The coverage of SWNT with a parylene layer successfully protected nanotubes from being damaged by the oxygen plasma.
Figure 4:
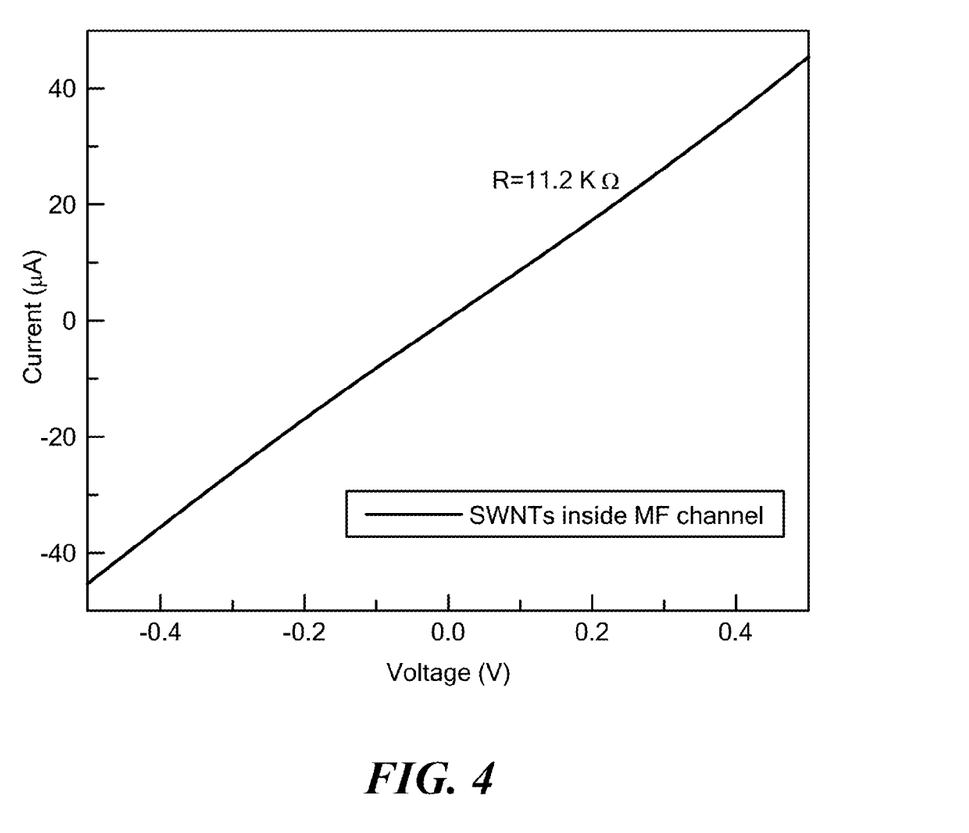
FIG. 4 shows the I-V characteristic of a SWNT sensor integrated inside a microfluidic channel.

In the second approach, the nanotubes were first assembled between the microelectrodes using the DEP process described above, which was performed prior to adding the microfluidic channel. While conducting the oxygen plasma treatment, a 10 μm thick parylene mask (fabricated according to Selvarasah et. al. [16]) was placed onto the chip, which prevented exposure of SWNT to the oxygen plasma required to bond the microfluidic channel. SEM images of SWNT assembled on microelectrodes before and after plasma treatment protected with the parylene mask were compared in FIGS. 3(a) and 3(b), respectively. Carbon nanotubes formed a network between the electrode (the bottom round shaped pad) and the substrate and the network was comprised of several SWNT bundles (FIG. 3(a)). No damage was observed to the SWNTs after plasma treatment in FIG. 3(b) with the protection of 10 μm parylene film. The shadow mask can be peeled off using either mechanical or chemical means. Mechanical means (pulling away the mask) are preferred, since chemical removal can leave an interfering chemical residue from the mask. After peeling off the shadow mask, the SWNT device was bonded with a PDMS microfluidic channel on a 150° C. hot plate for 15 min. The I-V characteristics of SWNT bonded with the microfluidic channel was measured and is illustrated in FIG. 4. The resistance of the SWNT decreased from 14 KΩ to 11 KΩ after bonding the microfluidic channel on a 150° C. hot plate. This was possibly due to reduction of the contact resistance between assembled SWNTs and metal electrodes caused by the thermal treatment [17].

Figure 5A:
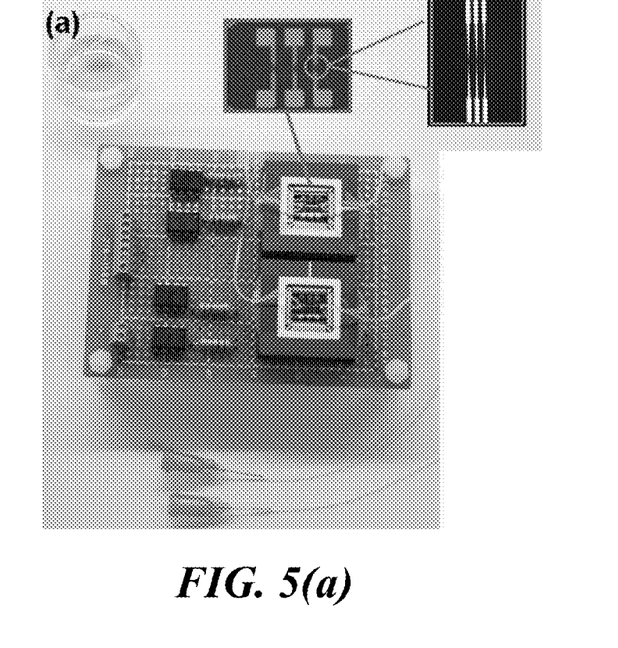
FIG. 5(a) shows a photographs of the testing board and the sensor array with a 3 µm gap between the electrodes enlarged in the insert micrograph.

The SWNT sensor integrated with microfluidic channel was next wire bonded onto a ceramic chip holder. As shown in FIG. 5(a), the fabricated device was mounted by means of the chip holder onto a circuitry board for signal conditioning (the corresponding circuitry is described in FIG. 5(c)). The change in resistance of the nanosensor caused by the presence of analytes (in this case, $H^+$) in the liquid sample was converted into a change in output voltage and transmitted, where the resistance of carbon nanotubes (Rswnt) was related to the output voltage by Equation 1 and Rswnt can be calculated by equation 2:

$$Rswnt/(Rswnt+R)=Vout/Vcc \quad (1)$$

$$Rswnt=R\times Vout/(Vcc-Vout) \quad (2)$$

Figure 5B:
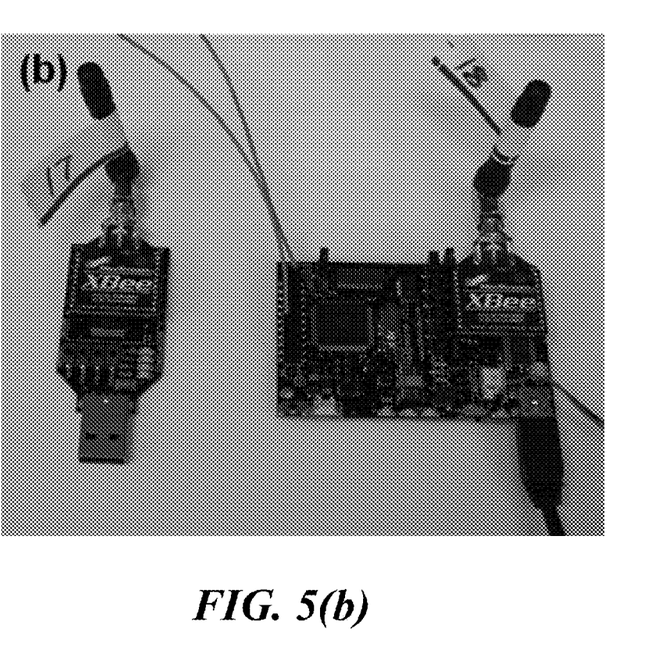
FIG. 5(b) shows a wireless transmission platform.
Figure 5C:
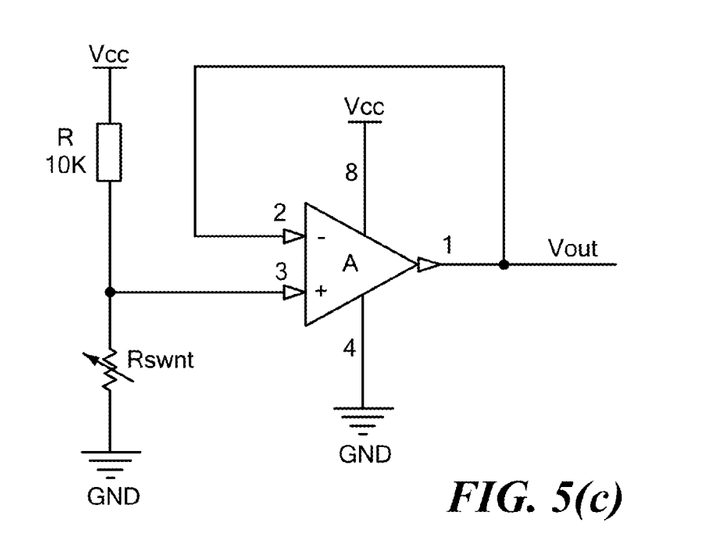
FIG. 5(c) is a schematic illustration of the testing circuitry for the SWNT sensor. The insert in FIG. 5(a) illustrates the pattern of the chip and the structure of the Au electrodes.

Rswnt is the resistance of the SWNT; R is an external reference resistor (10 KΩ); Vout is the output voltage and Vcc is the voltage of the power supply. A wireless sensing platform (Waspmote) was used to acquire the output voltage and wirelessly transmit the data to a remote receiver (as shown in FIG. 5(b)), which could be directly connected to a computer.

Figure 5D:
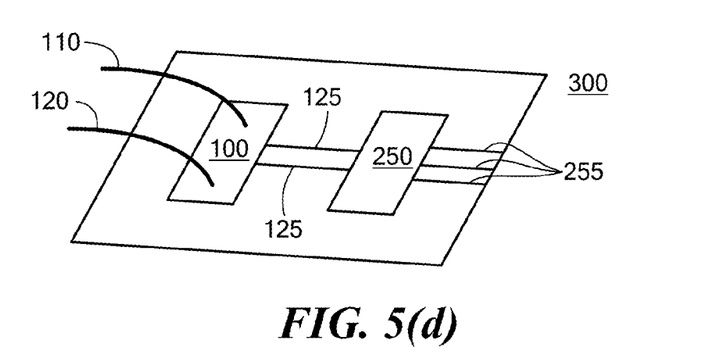
FIGS. 5(d)-5(f) show various configurations of the sensor device with different modes of outputting the results of the measurements.
Figure 5E:
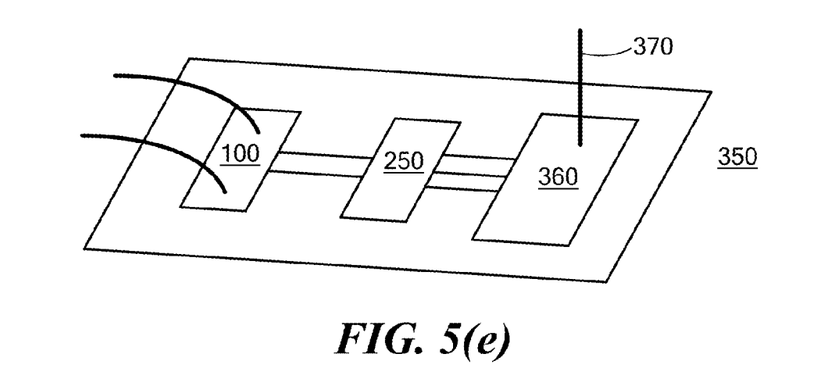
Figure 5F:
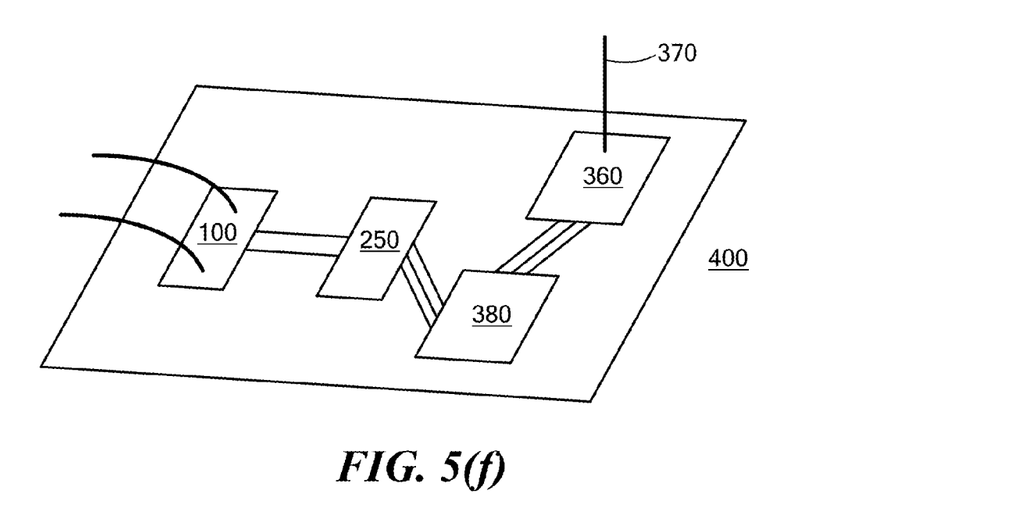

A sensor device according to the present invention can be configured in a number of different ways to suit the needs of the user. For example, the device can be incorporated into another device, such as an analytical device, a "lab on a chip" system, or it can be used as a stand-alone sensor. The sensor device can include only the nanosensor without any in-built detection circuitry, memory, or data processing circuitry, or it can optionally be configured to include, either on the same substrate (i.e., chip) or on an attached substrate, any one or more of the following optional components, or other components: a detection circuit, a data processing circuit, a wireless transmission module, an antenna, a microprocessor, a memory chip or hard drive, and a battery. The sensor device can be incorporated into a housing and be outfitted with a display, such as an analog or digital display to output a value of an electrical property of the sensor or a calculated or computed value of an amount or concentration of a chemical agent or analyte. FIG. 5(d) shows an embodiment (300) that includes sensor device 100 attached through one or more electrical leads 125 to detection circuit 255, which in turn has one or more output leads 255 that convey one or more output values off of the device. Input and output lines 110 and 120 provide a fluid pathway onto and off of the device for the sample liquid. FIG. 5(e) shows an embodiment (350) that further includes transmitter module 360, which transmits a signal, such as a radio frequency signal, from the device through antenna 370. FIG. 5(f) shows another embodiment (400) that includes data processing module 380 interposed between detection circuit 250 and transmitter 360. The data processing circuitry may also be combined with the detection circuit and/or the transmitter circuit into a single electrical module. Optionally, the data processing and/or detection circuits can be programmed through direct contacts, buttons or a touch screen display on the device, or remotely through a receiver module or combined transmitter/receiver module in conjunction with a cell phone, tablet computer, laptop computer, or remote computer system.

The sensor device can be supplied as the device alone or as a kit, with instructions for use, and optionally with one or more reagents, such as reagents for SWNT in situ functionalization, reagents for modifying the sample prior to detection, etc. Certain microfluidics embodiments can be preloaded with one or more reagents when supplied as a kit. The device can also be provided with microfluidics channel attached but lacking the SWNT sensor, which can be added by performing DEP with the user's own functionalized SWNT.

The pH value of water in rivers and lakes may change due to introduction of pollutants through human activities including automobile exhaust (generation of acid rain), accidental spills, agricultural run-off and sewer overflows. Infant fish and insect larvae are sensitive to low pH (acidic) aqueous environments, and extreme values of pH can be lethal to most organisms [18]. Monitoring the pH value of water is critical to provide an early warning to the environmental authorities. Due to the unique properties of nanomaterials, including carbon nanotubes, boron nitrite nanotubes, and grapheme, they have recently attracted considerable attention from researchers for the detection of pH value in water [19-21]. However, prior to the present invention, there does not appear to have been available a microfluidic system which is adapted for continuous pH monitoring at remote locations.

The fabricated nanosensor system was applied to detect pH values of aqueous solutions. The expected pH range in rivers is between 6.5 and 9.0 [22]. Therefore, buffers with pH values of 5, 6, 7, and 8 were prepared and calibrated using a commercial pH meter [Hach Inc.]. It is noted that the only effects of ions and molecules that can be sensed by SWNT-based sensors are those acting within the Debyelength. The Debye length in this case can be simply defined as the typical distance required by charged molecules surrounding the nanotubes to be sensed by the charge carriers inside the nanotubes, and it is inversely proportional to the square root of the ionic strength (I) in liquid [23]. In water, the Debye length is ~0.321 to 0.5 nm. In order to maintain the same Debye length for SWNT in the various pH buffer solutions, the ionic strengths of the pH buffer solutions were held constant at 100 mM. With the same Debye length in the different pH buffer solutions, the conductance of the SWNT was only affected by the pH values of solutions.

Figure 6:
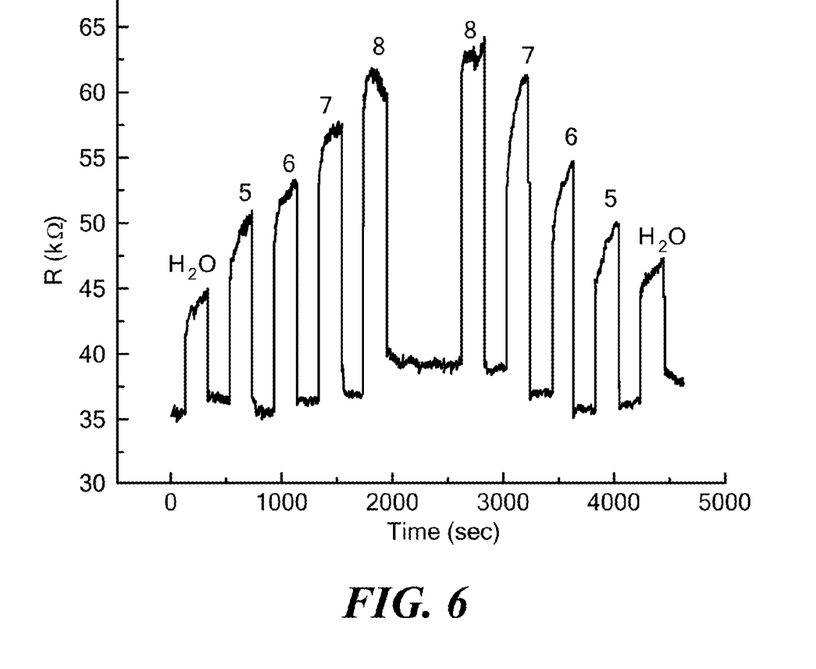
FIG. 6 shows the resistance of an SWNT sensor after exposure to deionized water and different pH buffers. The sensor was rinsed with deionized water and dried in air before introducing each different pH solution. The resistance of the SWNT dropped back to essentially the same value after each cycle of rinsing and drying, which indicated that the nanotubes were stable during pH sensing.
Figure 7:
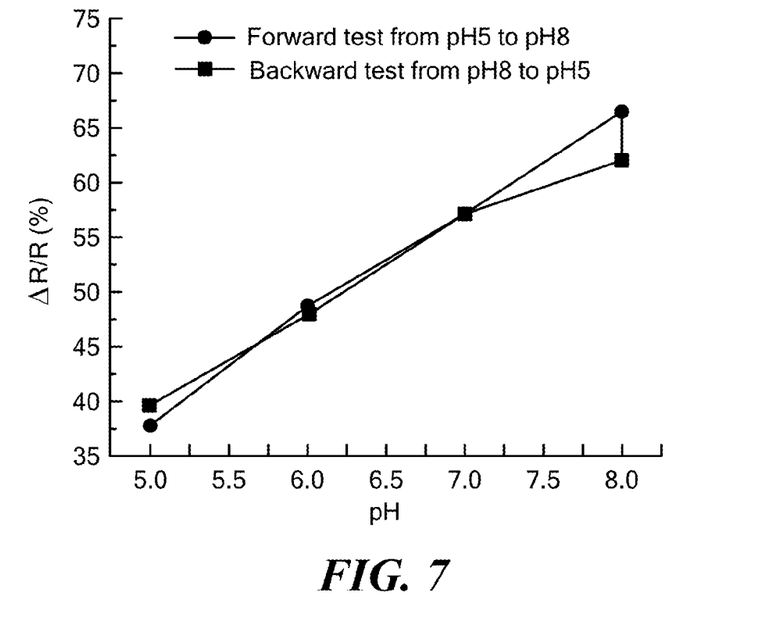
FIG. 7 shows the percentage change in resistance of carbon nanotubes measured in buffer solutions from pH 5 to pH 8 and from pH 8 to pH 5. The forward test (from pH 5 to pH 8) is plotted with round dots and the backward test (from pH 8 to pH 5) is plotted with square dots.

The output voltage of the nanosensor system during pH detection was recorded and converted back into the resistance of nanotubes by a computer. In FIG. 6, the SWNT resistance was plotted versus time, and the liquid to be tested was changed from deionized water to buffer solutions with increasing pH values, and then from buffer solutions with decreasing pH values back to deionized water. The resistance of the SWNT sensor increased from 50.26 k$\Omega$ to 61.54 k$\Omega$ when the pH values inside the microfluidic channel increased from 5 to 8. In addition, the forward measurement (pH values from 5 to 8) exhibited an opposite trend compared to the backward measurement (pH values from 8 to 5) which indicated that the response of SWNT nanosensor to pH was reversible and repeatable. Between each solution change, the SWNT sensor was rinsed with deionized water thoroughly and dried with compressed air. After the SWNT were washed and dried, the initial resistance of SWNTs was essentially recovered, which implied that SWNT sensor was able to maintain a considerable level of stability when utilized in a liquid environment. Moreover, when the changes in resistance of the SWNT sensor during exposure to different pH buffers were calculated and plotted in FIG. 7, the response of the sensor was essentially linearly proportional to the pH value of solutions inside the microfluidic channel.

Figure 8:
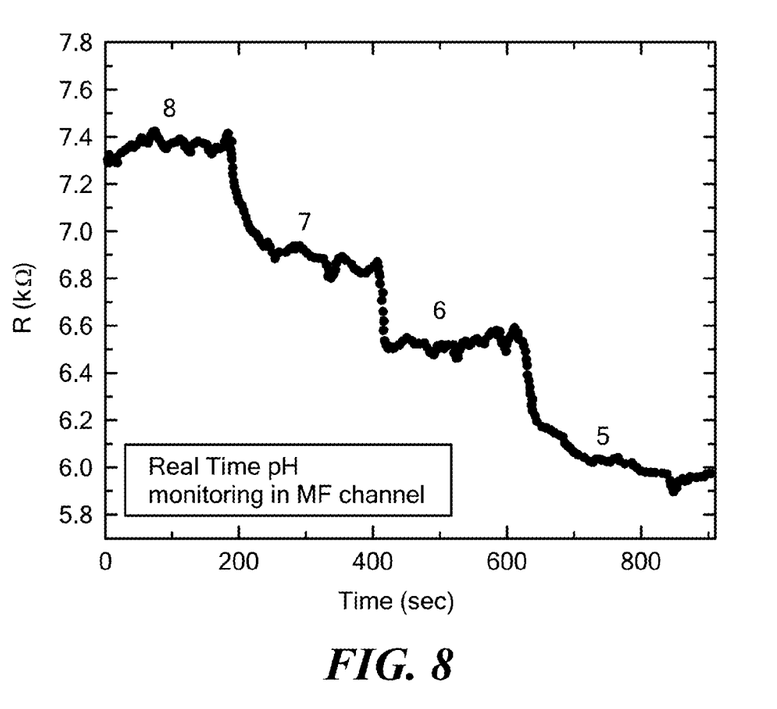
FIG. 8 shows the resistance of a SWNT sensor inside a microfluidic channel when exposed to aqueous solutions with different pH values. The buffer solution inside the microfluidic channel was continuously changed from pH 8 to pH 5 via a syringe. This test mimics real-time pH monitoring of a liquid sample.

The SWNT nanosensor integrated into a microfluidic system was tested during real-time pH monitoring under continuous sample liquid flow conditions. The resistance of the SWNT sensor was recorded as a function of time, during which the solution inside the microfluidic channel was changed to different pH buffers. As shown in FIG. 8, the resistance of the SWNT increased from 5.55 k$\Omega$ in deionized water to 7.27 k$\Omega$ after exposure to pH 8 buffer solution (the change in resistance was about 31%). When pH 7 buffer was introduced into the channel, the resistance of the nanotubes gradually decreased to 6.85 k$\Omega$. As the pH values of the solutions inside the channel decreased, the resistance of SWNT sensor decreased immediately and reached a stable value within a few seconds. The response of the microfluidics-integrated nanosensor to continuous pH changes showed the same trend as the data plotted in FIG. 6, obtained under fluid static conditions. In addition, this real-time measurement showed that the response time of the SWNT sensor to the pH value of the aqueous solution was less than 10 seconds. All the measurements described above were repeated three times with five different samples, and the results were confirmed.

The integration of a carbon nanotube-based sensor with a microfluidic system according to the present invention provides for continuous and remote monitoring of liquid samples, such as for water quality monitoring and for monitoring of fluids in biological systems including cell culture media and various fluid spaces in the bodies of living animals or body fluid samples taken from living animals. The SWNT-based sensor device has many superior properties compared to conventional detection equipment, and it has high sensitivity, fast response time, and is well suited for miniaturization of analytical devices. With the addition of one or more microfluidic sub-systems customized for liquid sampling, sample preparation, sample purification, or carrying out chemical pre-treatment of the sample before testing, the SWNT-based sensor can be utilized for autonomous monitoring in remote environments, such as for water quality monitoring.

The invention includes a method of detecting or quantifying a chemical agent or analyte in a liquid sample. Using a sensor device as described above, a liquid sample is allowed to flow into the microfluidic channel and to fill the enclosed gap (sensor chamber) of the device. The output signal, or a change in the output signal, is then observed using the detection circuit, either by directly probing the circuit, or by receiving an output value from a display on the device, or by receiving a value from the data processing module either directly, through display, or remotely via the wireless transmission system. The observed signal or change in signal is indicative of the presence or absence, or of the concentration or amount, of the chemical agent or analyte. If desired, the output signal can be compared to a calibration made with the same sensor device or a similar device in order to more accurately analyze the presence and/or concentration of the agent. Sampling and monitoring of results can be performed either continuously or intermittently, such as at predetermined times or intervals, as desired. As part of the sampling process, the sample liquid optionally can be separated, filtered, purified, or chemically modified using the microfluidics system.

One challenge in the integration of nanosensors and microfluidic systems is that the plasma treatment required for PDMS bonding would ordinarily damage the carbon nanotubes on the microdevice. In order to solve this problem, the inventors have developed two approaches by which an SWNT-based nanosensor can be fabricated inside of a microfluidic channel without damage to the sensing elements. First, the microfluidic channel can be bonded onto a substrate, such as a silicon substrate, and then the SWNT can be assembled via a dielectrophoretic process carried out inside the already fabricated microfluidic channel. Second, the SWNT can be assembled on the substrate and protected by a shadow mask, such as a parylene mask, during plasma treatment, after which the microfluidic channel is bonded onto the device, enclosing the SWNT sensor element. The SWNT-based microfluidic sensor was tested under continuous flow conditions and found to produce a linear relationship between the change in resistance of the nanosensor and the concentration of a chemical agent in the test liquid (e.g., $H^+$ concentration in buffered aqueous solutions). The sensing responses to analyte were reversible and repeatable. By connecting the sensor with a signal processing board and a wireless transmission unit, the SWNT-based sensor was shown to be functional as a remotely located independent sensing unit with a small size. This embodiment of the invention can be placed in rivers and lakes, and in various water transportation systems, such as household drains and pipes for real time water quality monitoring.

As used in any claim herein, "consisting essentially of" does not exclude materials or steps whose effects are immaterial with respect to the basic and novel characteristics of the claim. Any recitation herein of the term "comprising", particularly in a description of components of a composition or in a description of elements of a device, can be exchanged with "consisting essentially of" or "consisting of" to describe alternative embodiments.

While the present invention has been described in conjunction with certain preferred embodiments, one of ordinary skill, after reading the foregoing specification, will be able to effect various changes, substitutions of equivalents, and other alterations to the compositions and methods set forth herein. All publications cited herein are wholly incorporated by reference.

REFERENCES

[1] Glasgow H B, Burkholder J M, Reed R E, Lewitus A J and Kleinman J E 2004 Real-time remote monitoring of water quality: a review of current applications, and advancements in sensor, telemetry, and computing technologies *J Exp Mar Biol Ecol* 300 409-48

[2] Suehiro J, Zhou G B and Hara M 2005 Detection of partial discharge in SF6 gas using a carbon nanotube-based gas sensor *Sensor Actuat B-Chem* 105 164-9

[3] Rawson F J, Garrett D J, Leech D, Downard A J and Baronian K H R 2011 Electron transfer from *Proteus vulgaris* to a covalently assembled, single walled carbon nanotube electrode functionalised with osmium bipyridine complex: Application to a whole cell biosensor *Biosens Bioelectron* 26 2383-9

[4] Kaempgen M and Roth S 2006 Transparent and flexible carbon nanotube/polyaniline pH sensors *J Electroanal Chem* 586 72-6

[5] Roberts M E, LeMieux M C and Bao Z N 2009 Sorted and Aligned Single-Walled Carbon Nanotube Networks for Transistor-Based Aqueous Chemical Sensors *Acs Nano* 3 3287-93

[6] Forzani E S, Li X L, Zhang P M, Tao N J, Zhang R, Amlani I, Tsui R and Nagahara L A 2006 Tuning the chemical selectivity of SWNT-FETs for detection of heavy-metal ions *Small* 2 1283-91

[7] Zhou R H, Wang P and Chang H C 2006 Bacteria capture, concentration and detection by alternating current dielectrophoresis and self-assembly of dispersed single-wall carbon nanotubes *Electrophoresis* 27 1376-85

[8] Bhattacharya M, Hong S, Lee D, Cui T and Goyal S M 2010 Carbon nanotube based sensors for the detection of viruses *Sensor Actuat B-Chem* In press 8

[9] Whitesides G M 2006 The origins and the future of microfluidics *Nature* 442 368-73

[10] Toh Y C, Zhang C, Zhang J, Khong Y M, Chang S, Samper V D, van Noort D, Hutmacher D W and Yu H R 2007 A novel 3D mammalian cell perfusion-culture system in microfluidic channels *Lab Chip* 7 302-9

[11] Tan Y C, Fisher J S, Lee A I, Cristini V and Lee A P 2004 Design of microfluidic channel geometries for the control of droplet volume, chemical concentration, and sorting *Lab Chip* 4 292-8

[12] Liu J and Fu Q 2005 Integrated single-walled carbon nanotube/microfluidic devices for the study of the sensing mechanism of nanotube sensors *J Phys Chem B* 109 13406-8

[13] Bourlon B, Wong J, Miko C, Forro L and Bockrath M 2007 A nanoscale probe for fluidic and ionic transport *Nat Nanotechnol* 2 104-7

[14] Whitesides G M and McDonald J C 2002 Poly(dimethylsiloxane) as a material for fabricating microfluidic devices *Accounts Chem Res* 35 491-9

[15] Bhattacharya S, Datta A, Berg J M and Gangopadhyay S 2005 Studies on surface wettability of poly(dimethyl) siloxane (PDMS) and glass under oxygen-plasma treatment and correlation with bond strength *J Microelectromech S* 14 590-7

[16] Dokmeci M R, Selvarasah S, Chao S H, Chen C L, Sridhar S, Busnaina A and Khademhosseini A 2008 A reusable high aspect ratio parylene-C shadow mask technology for diverse micropatterning applications *Sensor Actuat a-Phys* 145 306-15

[17] Woo Y, Duesberg G S and Roth S 2007 Reduced contact resistance between an individual single-walled carbon nanotube and a metal electrode by a local point annealing *Nanotechnology* 18

[18] Howells G P 1994 *Water quality for freshwater fish*: Taylor & Francis)

[19] Zhao L P, Nakayama T, Tomimoto H, Shingaya Y and Huang Q 2009 Functionalization of carbon nanotubes with a pH-responsive molecule to produce a pH *sensor Nanotechnology* 20

[20] Huang Q, Bando Y, Zhao L, Zhi C Y and Golberg D 2009 pH sensor based on boron nitride nanotubes *Nanotechnology* 20

[21] Lei N, Li P F, Xue W and Xu J 2011 Simple graphene chemiresistors as pH sensors: fabrication and characterization *Meas Sci Technol* 22

[22] LCRA 2011 Water quality indicators-Key measures provide a snapshot of conditions ed E w a c s f C Texas (Austin, Tex.: Energy water and community services for Central Texas)

[23] Lustig S R, Jagota A, Khripin C and Zheng M 2005 Theory of structure-based carbon nanotube separations by ion-exchange chromatography of DNA/CNT hybrids *J Phys Chem B* 109 2559-66

What is claimed is:

1. A method of fabricating a sensor device for the detection of a chemical agent in a liquid sample, the method comprising the steps of:
   (a) depositing a conductive layer onto an insulating or semiconducting substrate, whereby the conductive layer forms a pattern comprising first and second microelectrodes and having a gap between the first and second microelectrodes;
   (b) forming a microfluidic channel that covers a portion of the substrate, encloses the gap, and is fluidically connected on one side of the gap to an inlet port and on another side of the gap to an outlet port;
   (c) flowing an aqueous suspension of single-walled carbon nanotubes (SWNT) through said inlet port to fill said enclosed gap with said aqueous suspension;
   (d) applying an AC voltage between the first and second microelectrodes, whereby one or more of the SWNT are dielectrophoretically assembled across the gap and form an electrical connection at one end of the one or more SWNT with the first microelectrode and at another end of the one or more SWNT with the second microelectrode; and
   (e) removing said aqueous suspension of SWNT from the microfluidic channel;
   wherein a plurality of the first and second microelectrode pair is formed, each pair having a gap between the microelectrodes of the pair, and the gap is enclosed by the microfluidic channel; and whereby one or more SWNT are dielectrophoretically assembled across each gap and form an electrical connection at one end of the one or more SWNT with the first microelectrode of each pair and at another end of the one or more SWNT with the second microelectrode of each pair;
   wherein steps (c) through (e) are repeated for one or more cycles of SWNT assembly; wherein at each performance of step (d) the voltage is applied between a different pair of the plurality of first and second microelectrode pairs;
   wherein for each performance of steps (c) and (d) the SWNT are differently functionalized, whereby a multiplex sensor is fabricated.

2. The method of claim 1, wherein step (b) comprises:
   (b1) forming the microfluidic channel in polydimethylsiloxane (PDMS) using SU-8 replica molding and photolithography;
   (b2) exposing the microfluidic channel and the substrate to an oxygen plasma for about 30 seconds;
   (b3) bonding the microfluidic channel to the substrate at about 150° C. for about 15 minutes.

3. The method of claim 1, further comprising:
   (f) attaching to the substrate a detection circuit connected to said first and second microelectrodes and capable of detecting a change in an electrical property of the one or more SWNT.

4. The method of claim 3, further comprising:
   (g) attaching to the substrate a wireless transmitter capable of transmitting an output signal from said detection circuit to a remote receiver.

5. The method of claim 3, further comprising:
   (g) attaching to the substrate a data processing module capable of processing an output signal from said detection circuit and outputting a signal that provides information on the presence and/or amount of said chemical agent.

6. The method of claim 5, further comprising:
   (h) attaching to the substrate a wireless transmitter capable of transmitting an output signal from said data processing module to a remote receiver.

* * * * *